US00PP08510P

United States Patent [19]

Moore

[11] Patent Number: Plant 8,510

[45] Date of Patent: Dec. 21, 1993

[54] BLACKBERRY — ARAPAHO CULTIVAR

[75] Inventor: James N. Moore, Fayetteville, Ark.

[73] Assignee: University of Arkansas, Fayetteville, Ark.

[21] Appl. No.: 951,131

[22] Filed: Sep. 25, 1992

[51] Int. Cl.[5] ..... A01H 5/00

[52] U.S. Cl. ..... Plt./46.1

[58] Field of Search ..... Plt./46.1

[56] References Cited

U.S. PATENT DOCUMENTS

P.P. 5,686 3/1986 Moore ..... Plt. 46.1

P.P. 6,679 3/1989 Moore ..... Plt. 46.1

OTHER PUBLICATIONS

Voss, Donald H., (1992) "Relating Colorimeter Measurement of Plant Color to the *Royal Horticultural Society Colour Chart*", HortScience vol. 27(12) pp. 1256–1260.

*Primary Examiner*—James R. Feyrer

[57] ABSTRACT

Description and specifications of a new and distinct blackberry variety which originated from seed produced by a hand-pollinated cross of Arkansas Selection 631 (non-patented) and Arkansas Selection 883 (non-patented) is provided. This new blackberry variety can be distinguished by its thornless canes with erect growth habit, its early ripening, and its excellent fruit flavor and firmness.

2 Drawing Sheets

SUMMARY OF THE INVENTION

The new and distinct variety of blackberry originated from a hand-pollinated cross of Arkansas Selection 631 (non-patented)×Arkansas Selection 883 (non-patented) made in 1982 at the Arkansas Agricultural Experiment Station Fruit Substation at Clarksville, Ark. The seeds resulting from this controlled hybridization were germinated in a greenhouse in the spring of 1983 and planted in a field on the Arkansas Agricultural Experiment Station in Clarksville, Ark. The seedlings fruited during the summer of 1985 and one, designated Ark. 1536, was selected for its early fruit ripening, thornless canes, erect growth habit, and high fruit quality.

During 1986, the original plant selection was propagated asexually from root cuttings at the above noted location and a test row of 20 plants was established. Subsequently, larger test plantings have been established with asexually multiplied plants at four additional locations in Arkansas and on state experiment stations in Alabama, California, Florida, Indiana, Kentucky, Louisiana, Mississippi, Missouri, South Carolina, Tennessee, and Texas.

The new variety has been asexually multiplied annually since 1986 by the use of root cuttings and by rooting softwood cuttings. It forms new plants from adventitious buds on most root cuttings, but is best propagated by rooting softwood cuttings. During all asexual multiplication, the characteristics of the original plant have been maintained and no aberrant phenotypes have appeared.

Test plantings over a wide geographic area have shown this new variety to be adapted to differing soil and climatic conditions. It has performed well in tests in the Southeast United States but is not cold hardy in northern states.

Plants of the new variety are moderately vigorous and row establishment following planting is more rapid than with other thornless varieties. Both primocanes and floricanes are erect in growth habit and the new variety is as erect as Navaho, the first truly erect thornless variety to be developed. The plants are genetically thornless, having the recessive genes for thornlessness derived from Merton Thornless. Plants and fruit are moderately tolerant to anthracnose (*Elsinoe veneta* (Burkh.) Jenkins), and plants appear immune to orange rust (*Gymnoconia peckiana* (Howe) Trott).

Fruit of the new variety ripens earlier than any extant thornless blackberry, being 10–14 days earlier than the thornless Navaho variety and 2 days earlier than the thorny Shawnee variety. Average ripening date is June 5 in central Arkansas. The harvest period is concentrated into a 3 week period in contrast to most blackberry varieties that produce for 4 to 5 weeks. Fruit yields are comparable to the Navaho cultivar but are less than yields of the Shawnee variety. Yields are consistent from year to year.

The fruit is short conic in shape, bright glossy black in color and medium in size (ca. 5.0 g). The fruit is firm at maturity, rating slightly less firm than the Navaho variety but more firm than the Shawnee variety. Storage quality of the fruit is comparable to the Navaho variety and superior to the Shawnee variety.

The fresh fruit rates high in flavor, being comparable to be Navaho variety which it most closely resembles and superior to the Shawnee variety. The flavor is sweet and mildly subacid, with a prominent aroma reminiscent of wild blackberries. Flavor is very similar to the Navaho variety and is sweeter and more aromatic that the Shawnee variety. The soluble solids concentration averages 9.1%, which is higher than most other blackberry varieties. Seed size is smaller than other thornless and most thorny blackberry varieties, averaging 2.7 mg/seed.

Fruit clusters are medium-large, cymose, and are borne on the periphery of the plant canopy, providing easy access to harvest. Flower fertility is high and clusters are well filled.

The new variety has been named the ARAPAHO cultivar.

BRIEF DESCRIPTION OF THE PHOTOGRAPHS

The accompanying photographs show typical specimens of the fruit and leaf of the new variety in color as nearly true as it is reasonably possible to make in a color illustration of this character.

DETAILED DESCRIPTION OF THE NEW VARIETY

The following is a detailed description of the botanical and pomological characteristics of the subject blackberry. Color data are readings from a Minolta Chroma Meter CR-200, version 3.0 which measures absolute chromaticity in tristimulus values X,Y, and Z as determined by the Commission Internationale de l'Eclairage (CIE Yxy). Calibration was performed using a standard white plate supplied by the manufacturer. These color data are supplemented with Royal Horticultural Society Colour Chart designations obtained by computer matching of electronic color readings to RHS color references.

Where dimensions, sizes, colors and other characteristics are given, it is to be understood that such characteristics are approximations of averages set forth as accurately as practicable.

The descriptions reported herein are from specimens grown at Clarksville, Ark. unless otherwise noted.

Plant:

*Size.*—Medium, erect.

*Growth.*—Vigorous, prolific suckering from crowns, good suckering from roots.

*Productivity.*—Medium and for duration of three weeks; consistent from year to year.

*Cold hardiness.*—Hardy to −24° C., similar to Navaho.

*Canes.*—Thornless, erect. Cane diameter: base 2.0 cm, midpoint 1.3 cm, terminal 0.3 cm. Internode length: base 4.8 cm, midpoint 8.3 cm, terminal 3.3 cm. Floricane color: base Y=16.9, x=0.3785, y=0.4121 Yellow-Green (152A); midpoint Y=19.49, x=0.3880, y=0.4242 Yellow-Green (152A); terminus Y=18.53, x=0.3898, y=0.4251 Yellow-Green (152A). Primocane color: base Y=11.31, x=0.3737, y=0.3733 Green-Brown (199A); midpoint Y=12.05, x=0.3737, y=0.3773 Yellow-Green (147A); terminus Y=14.91, x=0.3720, y=0.4115 Yellow-Green (148A). Date of primocane emergence, Julian 95.

*Disease resistance.*—Moderate to anthracnose; immune to orange rust.

Foliage:

*Leaves.*—Large. Mature leaf diameter 6.05 cm; length 7.74 cm. Color: Floricane base abaxial Y=18.94, x=0.3635, y=0.4056 Yellow-Green (148A); adaxial Y=9.45, x=0.3607, y=0.4044 Yellow-Green (147A); midpoint abaxial Y=17.70, x=0.3641, y=0.4010 Yellow-Green (148A); adaxial Y=9.54, x=0.3529, y=0.3932 Yellow-Green (147A); terminal abaxial Y=14.00, x=0.3694, y=0.3909 Yellow-Green (148A); adaxial Y=10.32, x=0.3670, y=0.3816 Yellow Green (147A). Primocane base abaxial Y=17.17, x=0.3563, y=0.4124 Yellow-Green (148A); adaxial Y=8.85, x=0.3433, y=0.4127 Yellow-Green (147A); midpoint abaxial Y=14.95, x=0.3498, y=0.4092 Yellow-Green (148A); adaxial Y=7.46, x=0.3340, y=0.3904 Yellow-Green (147A); terminal abaxial Y=18.40, x=0.3512, y=0.4128 Yellow-Green (147B); adaxial Y=9.83, x=0.3421, y=0.4106 Yellow-Green (147A).

Flowers:

*Date of bloom.*—First — Julian 106; 50% — Julian 118; Last — Julian 130.

*Blossom color.*—Y=65.99, x=0.3284, y=0.3299 Greyed-White (156D).

*Reproductive organs.*—Stamens — erect, numerous. Pistils — numerous. Pollen — normal and abundant.

*Number flowers per cluster.*—5 to 6.

*Number of petals per flower.*—6.

Fruit:

*Maturity.*—Early, 14 days before Navaho. Average ripe date is June 5. Average period of ripening is June 5 to June 27.

*Size.*—Medium, average 5.0 g, uniform. Diameter: primary fruit at equator 1.92 cm, base pole 1.72 cm, terminal pole 1.22 cm; secondary fruit equator 1.76 cm, base pole 1.42 cm, terminal pole 1.07 cm.

*Shape.*—Short conic, uniform.

*Color.*—Glossy black; Y=2.53, x=0.3170, y=0.3129 Black (202A).

*Drupelet size.*—Medium, 5.2 mm.

*Seed size.*—Small, 2.7 mg.

*Soluble solids.*—9.1%.

*pH.*—2.80.

*Processed quality.*—Very good, similar to Navaho, superior to Shawnee.

*Uses.*—Fresh and processed, jellies, jams.

The Variety

The most distinctive features of the variety are its thornless canes with erect growth habit, early ripening, and outstanding fruit flavor and firmness.

I claim:

1. A new and distinct variety of blackberry, substantially as illustrated and described, characterized by its thornless, erect growing canes, early ripening, firm fruit and excellent fruit flavor.

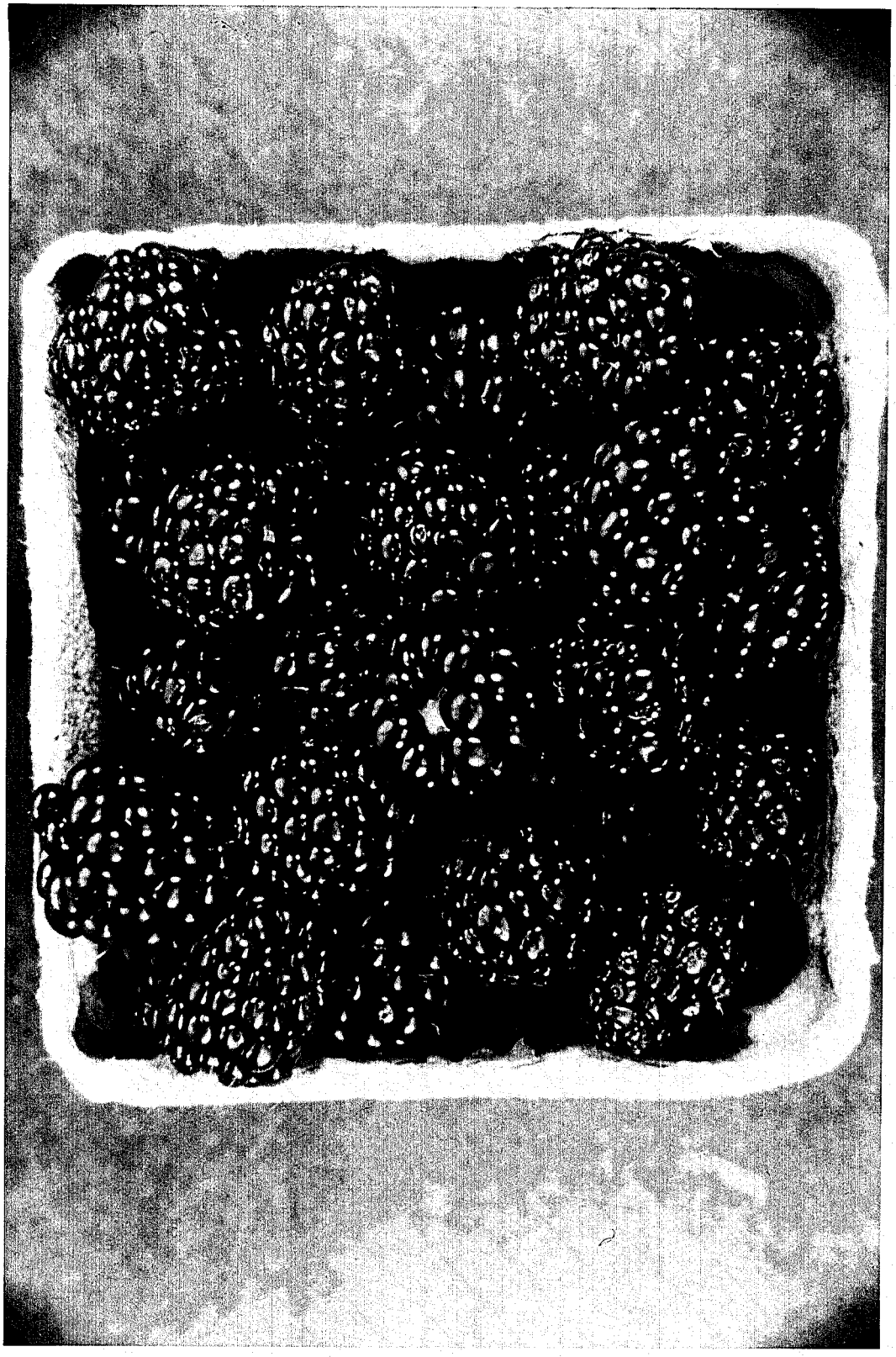

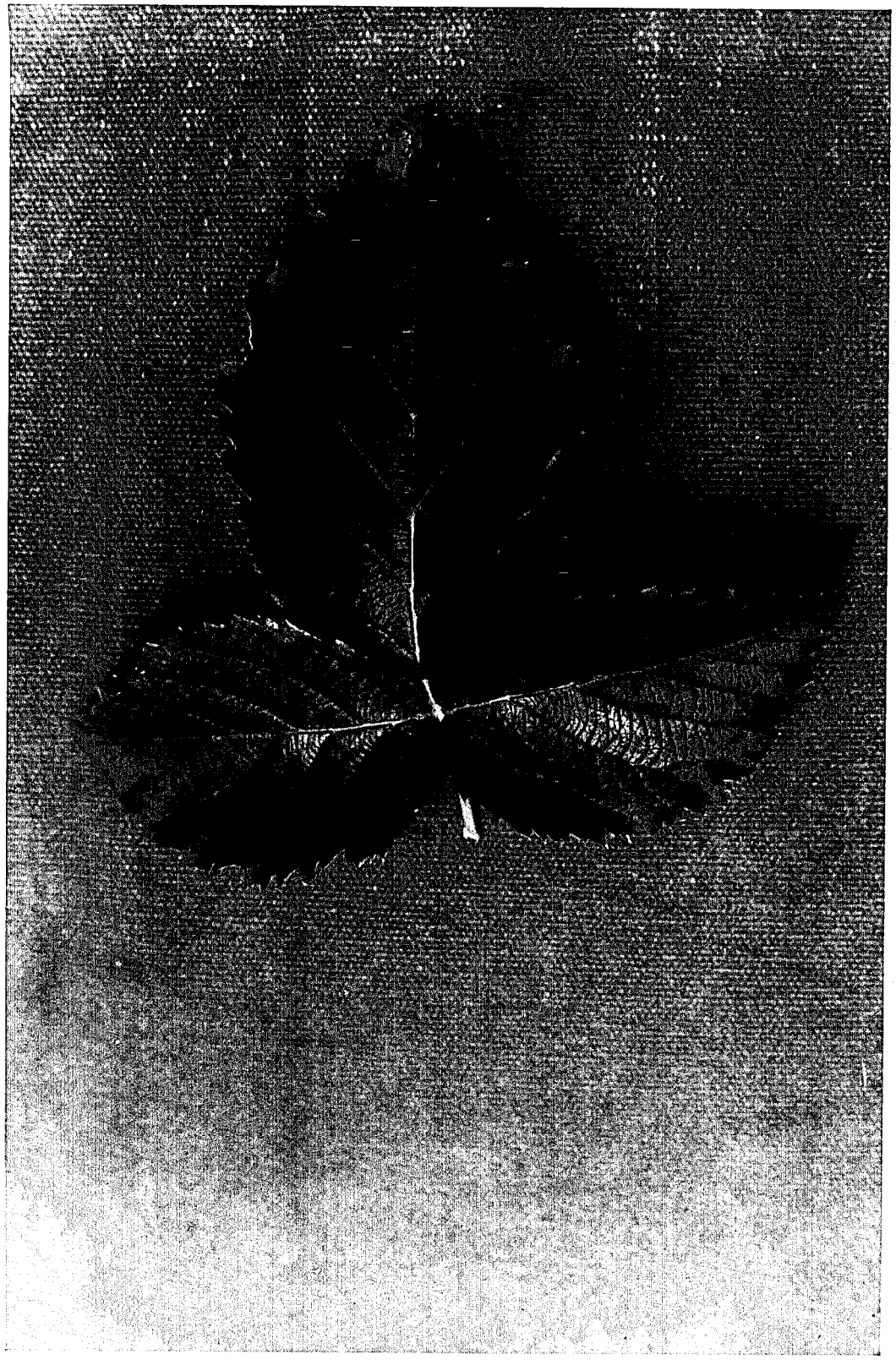

* * * * *